United States Patent [19]

Shapshay et al.

[11] Patent Number: 5,520,680
[45] Date of Patent: May 28, 1996

[54] METHOD FOR REMOVING AN ANIMAL ORGAN BY FACILITATING THE ATROPHY THEREOF

[75] Inventors: Stanley M. Shapshay, Boston; Michail M. Pankratov, Waltham, both of Mass.

[73] Assignee: New England Medical Center Hospital, Inc., Boston, Mass.

[21] Appl. No.: 493,648

[22] Filed: Jun. 22, 1995

[51] Int. Cl.$^6$ .................................................. A61B 17/36
[52] U.S. Cl. ................................ 606/12; 606/14; 604/20
[58] Field of Search ................................. 606/4, 12, 13, 606/14; 604/20

[56] References Cited

U.S. PATENT DOCUMENTS

| | | |
|---|---|---|
| 4,737,628 | 4/1988 | Lovoi . |
| 5,188,633 | 2/1993 | Kratzer et al. . |
| 5,207,668 | 5/1993 | L'Esperance, Jr. . |
| 5,207,672 | 5/1993 | Roth et al. . |
| 5,242,437 | 9/1993 | Everett et al. . |
| 5,380,317 | 1/1995 | Everett et al. . |

Primary Examiner—C. Fred Rosenbaum
Assistant Examiner—Perry E. Van Over
Attorney, Agent, or Firm—Wolf, Greenfield & Sacks

[57] ABSTRACT

A method is provided for facilitating the atrophying of a tonsil or adenoid ("organ") to cause the gradual removal thereof from the patient. A laser is positioned adjacent the organ, the wavelength for the laser being in the 700 nm to 1100 nm range and having energy sufficient to cause coagulation of blood in at least a significant number of the organ vessels over a period of several minutes, but not so much energy as to kill significant tissue of the organ or to cause significant damage to tissue adjacent to the organ. The laser is then turned on to irradiate the organ with laser energy and the entire exposed area of the organ is painted or otherwise irradiated. Irradiation continues until a selected condition of the organ, tissue adjacent the organ and/or laser source occurs. The organ may be cooled, for example by irrigation, during irradiation, and the organ may be insulated from surrounding tissue and/or an exogenous chromophore may be applied to the organ, the former to minimize damage to surrounding tissue and the latter to enhance absorption of laser energy by the organ.

18 Claims, 2 Drawing Sheets

METHOD FOR REMOVING AN ANIMAL ORGAN BY FACILITATING THE ATROPHY THEREOF

FIELD OF THE INVENTION

This invention relates to medical procedures for utilizing a laser to remove tonsils and/or adenoids, and more particularly to a medical procedure for performing tonsillectomies or adenoidectomies which involves using the laser to facilitate the atrophy of the organ rather than to kill the organ.

BACKGROUND OF THE INVENTION

Ideally, procedures for performing surgery to remove tonsils or adenoids (sometimes hereinafter collectively referred to as "organs") should be fast, should be as painless and non-traumatic as possible during surgery, should be painless after surgery, should be bloodless both during and after surgery and should facilitate rapid recovery of the patient. Rapid recovery includes absence of infection, minimum weight loss during the post-operative period, and a rapid return to normal activity. With current concerns on medical costs, the procedure should also be as inexpensive to perform as possible.

Unfortunately, current surgical procedures, which generally involve the use of a knife or other "cold" instrument, an electrocautery or a laser to separate the tonsil or adenoid, from surrounding tissue so that the organ can be physically removed, do not succeed in achieving any of these objectives. First, the pain and trauma level during surgery is such that these procedures must normally be performed under a general anesthesia. This significantly increases the cost of the procedure since it requires the services of an anesthesiologist and requires that the procedure be performed in a hospital operating room. The requirement to use a general anesthesia also increases the time required to perform the procedure, which normally lasts approximately thirty minutes, but may last significantly longer, can cause sickness and discomfort when the patient first comes out of the anesthesia, and in rare instances can result in the death of the patient. Further, since the procedure leaves an open wound, there may also be significant bleeding both during surgery and during the post-operative period, especially when the eschar falls off which may occur 3–5 days post-operative. For patients whose blood does not coagulate well, bleeding may occur for several days after the procedure, and in rare instances can even result in the death of the patient. Surgical procedures involving an open wound are a particular problem for hemophiliacs.

The wound created by the surgery also results in post-operative pain which, for a tonsil or adenoid procedure, is particularly noticed when the patient is swallowing. This pain makes it difficult for the patient to eat immediately after the procedure and may inhibit the ability of the patient to eat normally for several days thereafter. This can result in dehydration and weight loss for the patient; and the lack of good nutrition, coupled with the pain, can increase the time before the patient can return to normal activity.

Another potential problem with open wounds is infection. In order to prevent infection, patients are normally placed on antibiotics for some period of time after the surgery. In addition to the added cost of such antibiotics, it is known that increased use of antibiotics causes the development of infectious agents which are resistant to the antibiotics and makes it more difficult to treat the patient at a later date when the patient may have some type of serious, infectious illness.

Finally, there is the cost of such procedures. Even for a simple tonsillectomy or the combined removal of tonsils and adenoids, the cost for doctors and hospitals alone is in the $3,000.00 to $5,000.00 range. Since at least 340,000 tonsillectomies, either with or without adenoidectomies, are performed in the United States alone each year, making this the most frequently performed procedure in the United States, the total cost to the country is well over $1,000,000,000 a year and this does not include indirect costs such as lost work time and the like.

A need therefore exists for an improved procedure for removing tonsils and adenoids, which more closely approaches the ideal of being fast, painless, bloodless, low cost, and associated with rapid recovery. Such procedure should preferably be susceptible of performance in a doctor's office with no more than a local anesthetic and should be both safe to perform and simple to learn so as to minimize patient risk.

SUMMARY OF THE INVENTION

In accordance with the above, this invention provides a method for facilitating the atrophy of a tonsil or adenoid, which organ contains blood-filled vessels. The atrophy of the organ causes the gradual removal thereof from the patient. In general, the first step in the operation is to position a source of laser energy having a wavelength in the 700 nm to 1100 nm range adjacent to, but not touching, the organ. The laser should have an energy sufficient to cause coagulation of blood in at least a significant number of the organ vessels over a period of several minutes, but not so much energy as to kill significant tissue of the organ or to cause significant damage to tissue adjacent to the organ on which the laser might spuriously impinge. The energy of the laser source may for example be in a range from 5 watts to 15 watts. The laser source is then turned on to irradiate the organ with laser energy and either the laser source is moved relative to the organ during irradiation to paint the entire exposed area of the organ or the entire exposed area of the organ is otherwise irradiated. The moving step is preferably performed by providing an optical fiber with its proximal end attached to receive light from a laser and its distal end moved relative to the organ in the area adjacent thereto. For tonsillectomies and adenoidectomies, the distal end of the fiber is passed into the area adjacent to the tonsil or adenoid through the patient's mouth. At least one selected parameter of at least one of the organ, tissue adjacent to the organ and/or the laser source are monitored during irradiation and irradiation is terminated on the detection of a selected condition for the monitored parameter or parameters.

The selected parameters may include the color of the organ, with the selected condition in this case being the color of the organ becoming at least slightly blanched over substantially all of its exposed area. The selected parameter may also be the temperature of surrounding tissue, the selected condition being the temperature reaching a value above which damage to surrounding tissue might occur; or may be the temperature of the organ reaching a value at which either coagulation of the required number of organ vessels should occur or damage to the organ might occur. Finally, the parameter may be time of irradiation, with the selected condition being the irradiation for a period sufficient for coagulation of the desired number of organ vessels to occur.

The method preferably includes the step of cooling the organ during irradiation by for example irrigating the organ with a saline solution during this step. Prior to the irradiation step, it is desirable that the tissue surrounding the organ be insulated, for example by injecting a saline solution adjacent to the organ at the junction between the organ and surrounding tissue. For a tonsillectomy, the saline solution is injected into the space between the tonsil and the neck muscles. It is also desirable that a local anesthetic be administered to the organ and surrounding tissue prior to irradiation. Finally, for at least one embodiment, an exogenous chromophore is applied to the organ prior to irradiation, the chromophore being one which efficiently absorbs energy at the wavelength of the laser energy. Where the laser source includes a diode laser operating at a wavelength in 785 nm to 815 nm range, the exogenous chromophore may be indocyanine green (ICG) dye.

The foregoing other objects, features and advantages of the invention will be apparent from the following more particular description of a preferred embodiment of the invention as illustrated in the accompanying drawings.

IN THE DRAWINGS

DETAILED DESCRIPTION

Figure 1:
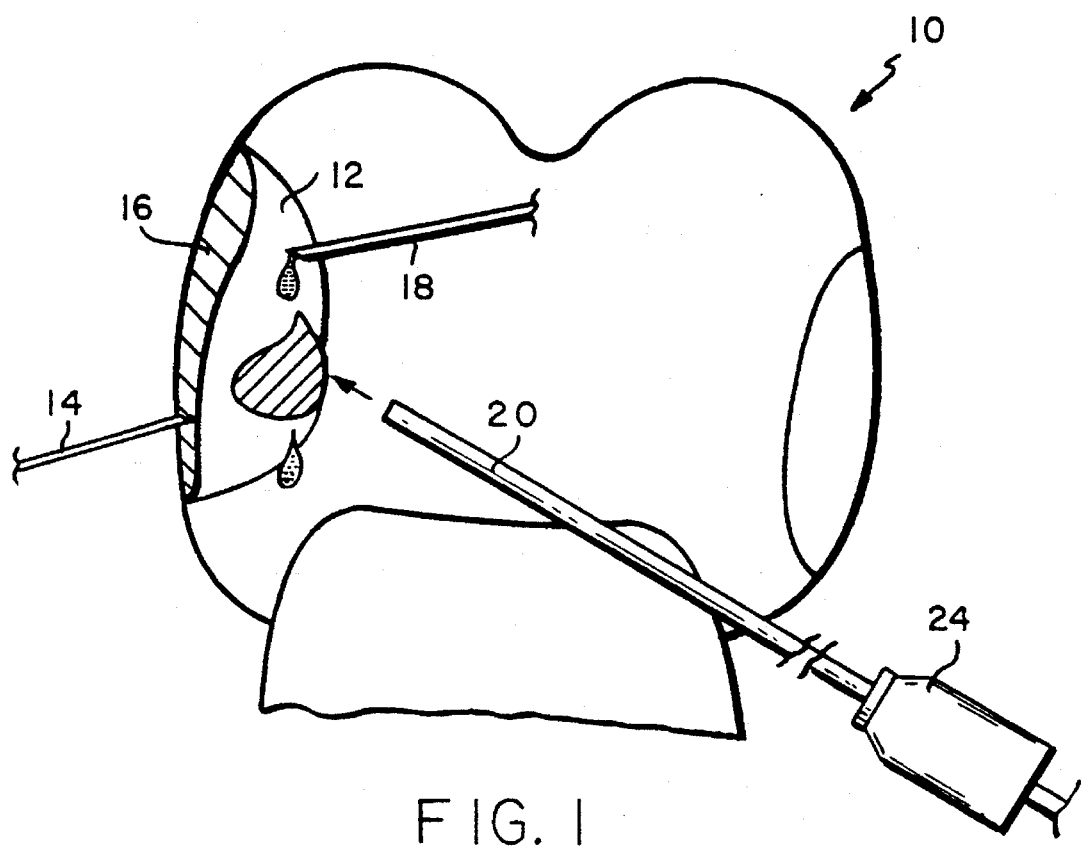
FIG. 1 is a diagrammatic view of a patient's throat illustrating various procedures performed on a patient's thyroid.

FIG. 1 shows the throat area 10 of a patient with tonsil 12 being attached to one wall thereof. Shown also are a needle 14 for injecting an exogenous chromophore, and in particular an indocyanine green (ICG) dye in the area 16 between the tonsil and the neck of the patient. A tube or needle 18 is also provided for irrigating the tonsil 12 with a saline or other suitable solution and an optical fiber 20 is provided which is connected to a diode or other suitable laser 24. Needle 14, tube 18 and fiber 20 are all moved to the positions shown for a preferred embodiment through the patient's mouth.

The laser utilized should have a wavelength in the 700 nm to 1100 nm range and should have an energy in the range of roughly 5 to 15 watts. For a preferred embodiment, the laser utilized was a diode laser having a wavelength of 810 nm and a power of 10 to 12 watts. While continuous wave lasers are used for a preferred embodiment, this is not a limitation on the invention and pulsed lasers could also be utilized.

The laser wavelength is selected so as to be above the optimum absorption range for blood, which is typically less than 600 nm and the energy is in the range indicated so as to permit energy to be more slowly absorbed in the vessels of the organ, thereby resulting in coagulation of the blood in such vessels, but not in the bursting or destruction thereof.

Figure 2:
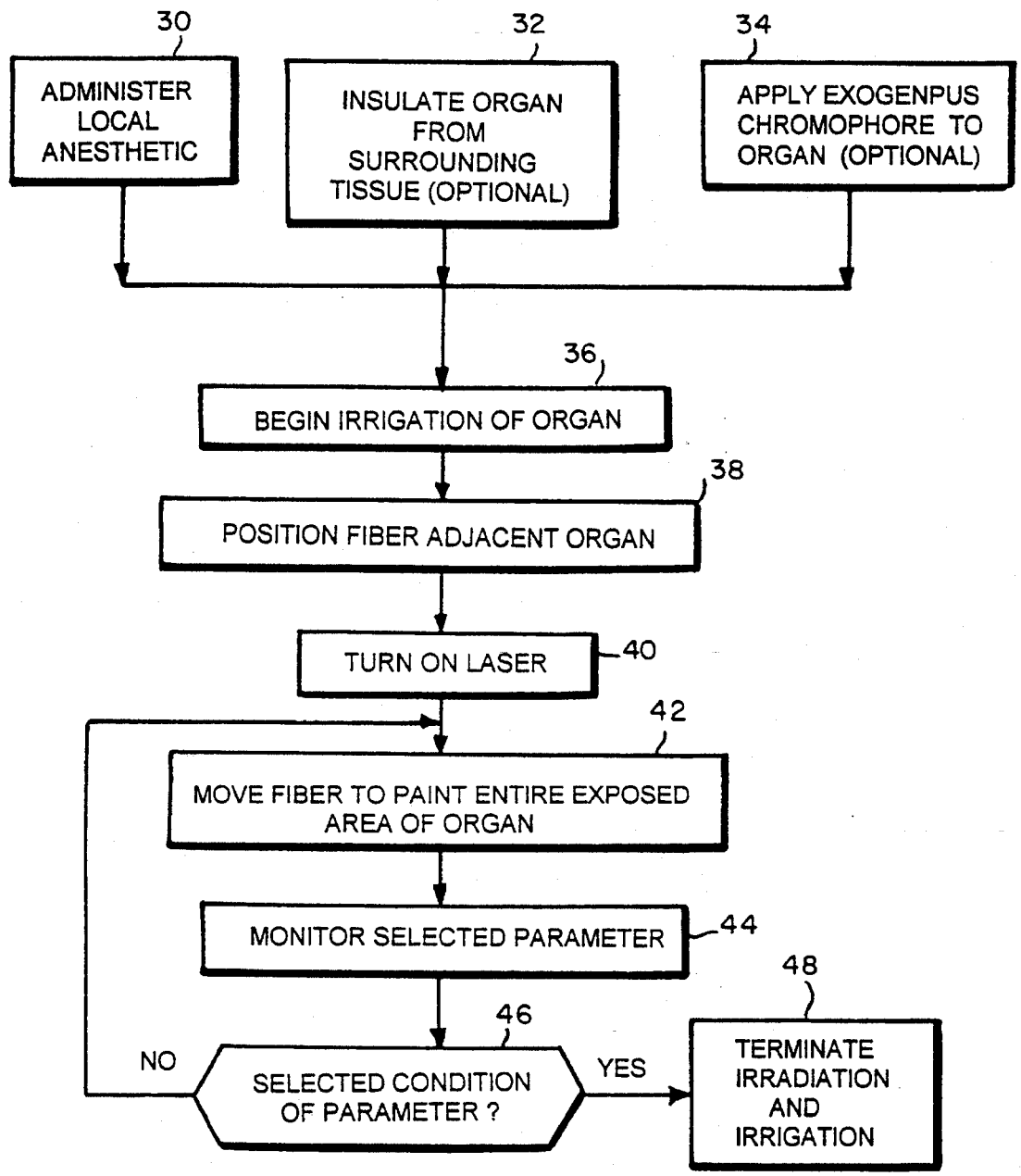
FIG. 2 is a flow diagram of the procedure for treating a patient to remove a tonsil or adenoid in accordance with the teachings of this invention.

In operation, three preliminary steps may be performed, steps 30, 32 and 34 (FIG. 2), all of which are optional. During step 30, an anesthetic is administered to the patient which anesthetic is preferably local. While this step would normally be performed, since the objective of the procedure is not to destroy tissue, depending on a patient's threshold of pain, the procedure can be performed without anesthetic, particularly for patients who may have an allergic reaction to anesthetic.

During step 32, the tonsil 12 or adenoid is insulated from surrounding tissue. For a preferred embodiment, this is accomplished by utilizing needle 14 to inject a saline solution into the gap 16 between the tonsil or adenoid and the wall of the neck or other surrounding tissue. The saline solution in the area 16 minimizes the transfer of heat from the organ to the surrounding tissue, thereby minimizing damage to such surrounding tissue, and in particular preventing any damage to the carotid artery which is in the neck adjacent the tonsils. Injury to the carotid artery, and in particular rupture thereof, could result in serious injury or even death to the patient. The insulating effect of the saline solution in area 16 may be enhanced by slightly cooling the solution before injection thereof. Other biocompatible solutions having good heat insulating properties could be substituted for the saline solution during step 32 or other techniques such as some type of solid insulator positioned in area 16 or a cryogenic technique might be used to minimize damage to surround tissues. While, if the power of the laser beam applied through fiber 20 is low enough, there may be insufficient heat transferred to surrounding tissue to require step 32, and this step is therefore optional, it is considered preferable that this step be performed to minimize any patient risk.

During step 34, an exogenous chromophore is applied to the tonsil or adenoid. The purpose of step 34 is to enhance uptake of the laser energy beam utilized by the target tissue, in this case the tissue of the tonsil or adenoid. This has the effect of minimizing adjacent tissue damage and reducing overall laser energy requirements. For a preferred embodiment, indocyanine green (ICG) dye was used as the exogenous chromophore, ICG having a high affinity for light in the 785–815 nm wavelength range, and therefore providing preferential absorption for laser energy in the 810 nm range of the diode laser utilized for the preferred embodiment. For the illustrative embodiment, the ICG dye was injected into the loose tissue in area 16 between the tonsilar capsule and the pharyngeal muscle, a place where the local anesthetic is normally injected. The dye could also be injected directly into the tonsil/adenoid, could be painted thereon or otherwise applied. However, while it is clear that performing step 34 prior to laser irradiation does reduce the laser power required to achieve desired results, and therefore minimizes damage to surrounding tissue, perhaps making step 32 unnecessary, it is not yet clear whether the advantages of this step are sufficient to warrant the complexity which this step adds to the operation, and this step is therefore also indicated as optional, although it may be preferred for at least some applications.

Steps 30–34, to the extent they are performed, may be performed in any order, and the particular order in which these steps are performed does not form part of the present invention. Once these preliminary steps have been performed, the operation proceeds to step 36 to begin the irrigation of the tonsil/adenoid with a saline or other biocompatible solution through tube 18, and to step 38 to move optical fiber 20 through the patient's mouth to a position adjacent the tonsil/adenoid. The order in which steps 36 and 38 are performed is also not critical. The irrigation of the tonsil/adenoid during step 36 and for the remainder of the procedure keeps the organ moist and prevents mucosa from parching. In particular, the surface of the organ is slightly cooled by the irrigation so as to permit coagulation of vessels through substantially the entire organ without destroying surface vessels.

When steps 36 and 38 have been completed, the operation proceeds to step 40 to turn on laser 24, causing laser energy to be applied through fiber 20 to the organ. Fiber 20 would typically be positioned roughly 3 to 5 mm from the surface of the organ during irradiation to form a 2.5 to 3.0 mm spot on such surface. During step 42, fiber 20 is moved over the surface of the tonsil/adenoid so as to paint the entire exposed area of the organ. While the painting procedure could be mechanized, typically it would be performed by the medical personnel performing this procedure, with such personnel observing the organ during the irradiation process and moving fiber 20 to paint areas which do not show blanching as the irradiation proceeds so as to achieve substantially uniform blanching of the organ. Alternatively, while a relatively small fiber in the range of approximately 1.0 mm was used for a preferred embodiment, resulting in a relatively small diameter beam impinging on the organ, a larger fiber could be utilized to achieve a larger diameter beam, or the beam could be passed through some form of beam diverging optics before impinging on the organ, so as to permit substantially the entire organ to be irradiated without the need for moving the fiber during step 42. If this were done, it might be desirable to increase the laser power slightly, and it might be desirable to pulse the laser rather than operating it in a continuous wave mode.

While irradiation is occurring, a selected parameter is being monitored (step 44) and during step 46 a determination is made as to whether a selected condition exists for the parameter. For a preferred embodiment, the parameter is the color of the organ, with the selected condition being slight mucosal blanching over substantially the entire exposed surface of the organ. Depending on the laser power utilized, such blanching normally occurs in approximately four to six minutes using the laser powers previously discussed, with the time required for the procedure being reduced when step 34 is performed prior to irradiation. Other conditions which might be monitored, either in addition to or instead of the color of the organ, are the temperature of the organ, the temperature of surrounding tissue, and/or the time of irradiation. For one of the temperature measurements, a suitable temperature monitor would be positioned at the location prior to irradiation and the condition detected during step 46 would be the temperature reaching a predetermined threshold. These detections might be in addition to a time or color detection as a failsafe against tissue damage in the monitored area.

So long as the selected condition is not detected, irradiation of the organ, including steps 42 and 44, continue to be performed. When the selected condition is detected during step 46, the operation proceeds to step 48 to terminate irradiation, typically by turning off the laser and by removing fiber 20 from proximity to the organ, and to terminate irrigation through tube 18. Once step 48 has been performed, the organ remains in the body but begins to atrophy. In particular, after the completion of the procedure, there is no blood or wound for the patient and, except for the blanched organ, there are no visible signs that the procedure has been performed. Once the patient recovers from anesthesia with little, if any, pain, the patient is typically able to both swallow and eat normal within a short time after the procedure is completed. This facilitates recovery since it prevents weight loss and dehydration after the procedure and facilitates a quick return to normal activities. The lack of an open wound also minimizes the likelihood of infection.

It is preferable that the patient be monitored at regular intervals once the procedure has been completed to be sure that the tonsil/adenoid is in fact atrophying, with a significant reduction in bulk normally being observable within seven days. If after two to three weeks, it appears that the atrophying of the organ is not proceeding at a desired rate, the procedure may be repeated to coagulate remaining tonsilar or adenoidal tissue. For large organs, multiple treatments may be part of the protocol so as to avoid overtreatment of the organ surface during the initial treatment. By forty-five days after completion of the procedure, all of the tonsil/adenoid should have completely atrophied and have disappeared without leaving any wound, scab, or the like on the wall of the neck.

An improved procedure for removing tonsils and adenoids is thus provided which is faster and less expensive than existing procedures while also being less painful and traumatic to the patient, both during the procedure and post-operatively, providing more rapid recovery and better patient nutrition during recovery. While the procedure has been described above with reference to a preferred embodiment, and certain variations on the preferred embodiment have also been discussed, it is apparent that these and other variations in the procedure could be made by those skilled in the art while still remaining within the spirit and scope of the invention.

What is claimed is:

1. A method for facilitating the atrophy of a tonsil organ or an adenoid organ, which organ contains blood filled vessels to cause the gradual removal of the organ, the method comprising the steps of:

positioning a source of laser energy having a wavelength in the 700 nm to 1100 nm range adjacent to, but not touching the organ, the laser having an energy sufficient to cause coagulation of blood in at least a significant number of the organ vessels over a period of several minutes, but not so much energy as to kill significant tissue of the organ or to cause significant damage to tissue adjacent the organ on which the laser might spuriously impinge;

irradiating the organ with laser energy from the source;

monitoring at least one selected parameter of at least one of the organ, tissue adjacent the organ and the laser source; and terminating irradiation on the detection of a selected condition for the monitored at least one parameter.

2. A method as claimed in claim 1 wherein at least one of the selected parameters is color of the organ, and wherein the selected condition is the color of the organ becoming at least slightly blanched over substantially all of said exposed area.

3. A method as claimed in claim 1 wherein at least one of the selected parameters is temperature of surrounding tissue, and wherein the selected condition is the temperature reaching a selected value above which damage to the surrounding tissue might occur.

4. A method as claimed in claim 1 wherein at least one of the selected parameters is temperature of the organ, and wherein the selected condition is the temperature of the organ reaching a value at which at least one of coagulation for said at least a significant number of the organ vessels should occur and significant damage to the organ might occur.

5. A method as claimed in claim 1 wherein at least one of the selected parameters is time of irradiation by the laser source; and wherein the selected condition is the irradiation being performed for a period sufficient for coagulation of said at least significant number of the organ vessels to occur.

6. A method as claimed in claim 1 including the step cooling the organ during irradiation.

7. A method as claimed in claim 6 wherein said cooling step includes the step of irrigating the organ with a saline solution during the irradiation step.

8. A method as claimed in claim 1 including the step performed at some time prior to the irradiation step of insulating surrounding tissue from the organ.

9. A method as claimed in claim 8 wherein said insulating step includes the step of injecting a saline solution adjacent to the organ at the junction between the organ and surrounding tissue.

10. A method as claimed in claim 1 including the step performed at some time prior to the irradiation step of administering a local anesthetic to the organ and surrounding tissue.

11. A method as claimed in claim 1 including the step performed at some time prior to the irradiation step of applying to the organ an exogenous chromophore which efficiently absorbs energy at the wavelength of said laser energy.

12. A method as claimed in claim 11 wherein the laser source includes a diode laser operated at a wavelength in the 785 nm to 815 nm range, and wherein the exogenous chromophore is indocyanine green (ICG) dye.

13. A method as claimed in claim 1 wherein the energy of the laser source is in a range from 5 watts to 15 watts.

14. A method as claimed in claim 1 wherein the positioning step includes the step of passing the distal end of an optical fiber connected at its proximal end to a laser through a patient's mouth to a position adjacent the selected organ.

15. A method as claimed in claim 1 wherein said irradiation step is performed over the entire exposed area of the organ.

16. A method as claimed in claim 15 wherein said irradiation step includes the step of moving the source relative to the organ during irradiation to paint the entire area of the organ which is exposed to the laster source.

17. A method as claimed in claim 1 wherein the method is repeated at least once for a given organ, there being at least a selected time interval between each performance of the method.

18. A method as claimed in claim 1 including the steps of monitoring the atrophying of the organ at intervals after the termination step, and repeating the method if the organ is found not to be atrophying at the desired rate.

* * * * *